United States Patent
Yoon

[11] Patent Number: 5,395,342
[45] Date of Patent: Mar. 7, 1995

[54] ENDOSCOPIC PORTAL

[76] Inventor: InBae Yoon, 2101 Highland Ridge Dr., Phoenix, Md. 21131

[21] Appl. No.: 557,869

[22] Filed: Jul. 26, 1990

[51] Int. Cl.$^6$ .................. A61B 17/32; A61B 19/00
[52] U.S. Cl. .................. 604/167; 604/164; 604/165; 604/248
[58] Field of Search ............ 604/158, 159, 160, 161, 604/162, 163, 164, 165, 166, 167, 168, 169, 170, 248, 264

[56] References Cited

U.S. PATENT DOCUMENTS

| | | | |
|---|---|---|---|
| 3,747,812 | 7/1973 | Karman et al. | 604/236 |
| 3,788,318 | 1/1974 | Kim et al. | 604/164 |
| 3,789,852 | 2/1974 | Kim et al. | 604/164 |
| 3,833,003 | 9/1974 | Tarricco | 604/164 |
| 4,187,849 | 2/1980 | Stim | 604/248 |
| 4,524,770 | 6/1985 | Orandi | 604/160 |
| 4,535,773 | 8/1985 | Yoon | 604/169 |
| 4,601,710 | 7/1986 | Moll | 604/165 |
| 4,654,030 | 3/1987 | Moll et al. | 604/165 |
| 4,668,221 | 5/1987 | Luther | 604/164 |
| 4,735,614 | 4/1988 | Yapp et al. | 604/165 |
| 4,769,005 | 9/1988 | Ginsburg et al. | 604/164 |
| 4,790,817 | 12/1988 | Luther | 604/164 |
| 4,808,168 | 2/1989 | Warring | 604/248 |
| 4,902,280 | 2/1990 | Lander | 604/165 |
| 4,919,653 | 4/1990 | Martinez et al. | 604/164 |
| 4,931,042 | 6/1990 | Holmes et al. | 604/164 |
| 4,943,280 | 7/1990 | Lander | 604/169 |
| 5,030,206 | 7/1991 | Lander | 604/164 |
| 5,053,016 | 10/1991 | Lander | 604/169 |

FOREIGN PATENT DOCUMENTS 1024410  3/1966  United Kingdom ............ 604/169

*Primary Examiner*—Gene Mancene
*Assistant Examiner*—Frank A. LaViola

[57] ABSTRACT

An endoscopic portal includes a valve assembly disposed at an open proximal end of a sleeve or cannula providing access to an internal operative site, the valve assembly having a passage therethrough of variable size to engage surgical instruments passing therethrough in sealing relation to prevent flow or leakage of fluid through the valve assembly.

14 Claims, 1 Drawing Sheet

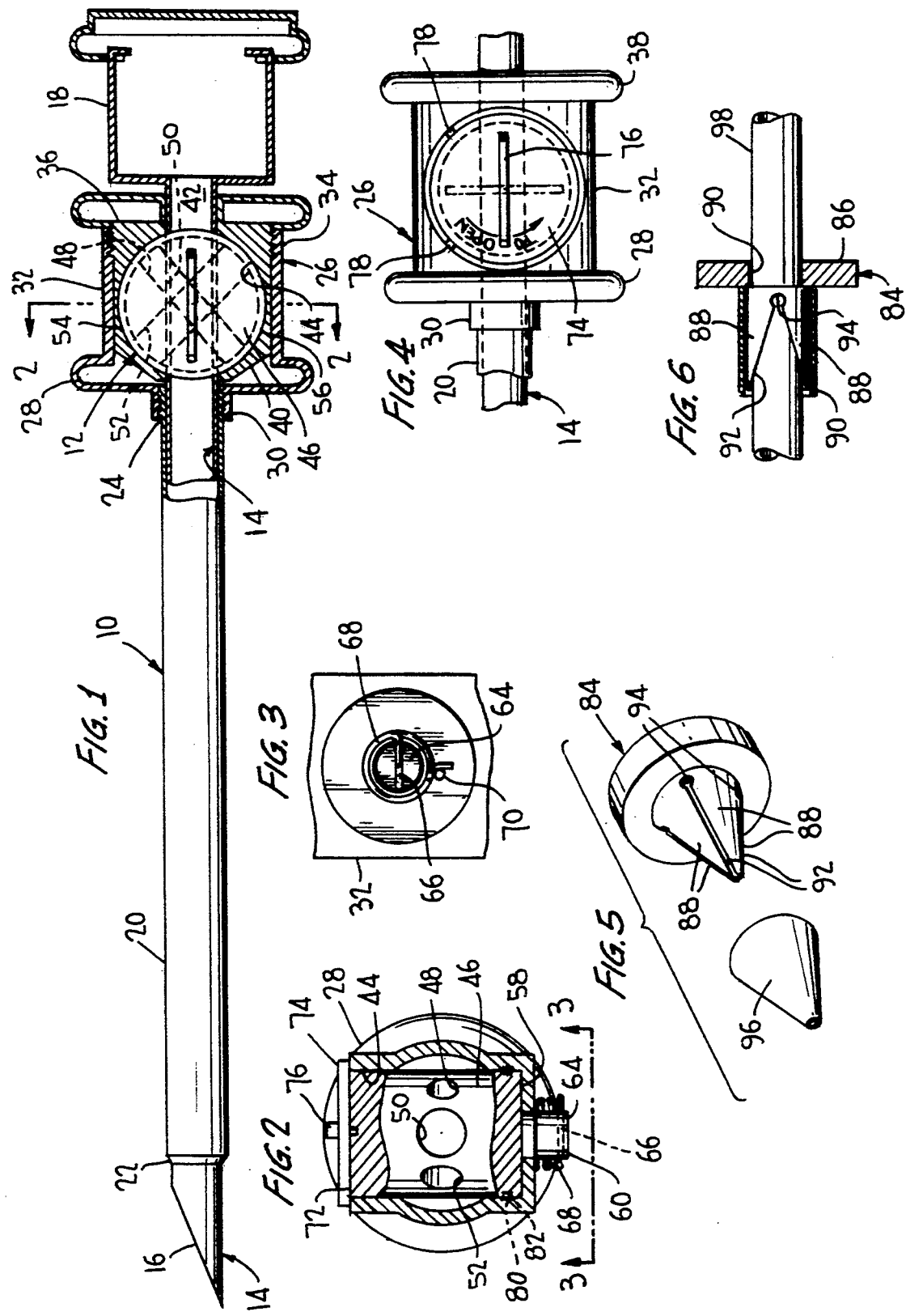

ENDOSCOPIC PORTAL

BACKGROUND OF THE INVENTION

1. Field of the Invention

The present invention pertains to endoscopic surgical instruments and, more particularly, to a valve assembly for providing a variable size passage in an endoscopic portal to prevent fluid flow through the valve while allowing surgical implements of various sizes to be selectively introduced through the valve.

2. Description of the Prior Art

Surgical procedures involving the placement of an endoscopic portal, such as a sleeve or cannula, through a body wall to provide a passage for insertion of surgical instruments frequently require that the passage be sealed to prevent the flow of fluids through the endoscopic portal. For example, many medical procedures gain access to the interior of an anatomical cavity by utilizing a surgical puncturing or penetrating instrument, such as a trocar, obturator or needle, having a sharp penetrating point for puncturing or penetrating the cavity wall to establish communication with the interior of the anatomical cavity. A sleeve or cannula is then left in situ for utilization as a portal to introduce surgical instruments into the anatomical cavity. Because it is necessary to prevent fluid flow to and from the surgical site, the portal must be sealed prior to and subsequent to the introduction of surgical instruments and while such instruments are in place. Furthermore, fluids, such as gaseous phase carbon dioxide or nitrous oxide, may be introduced into the anatomical cavity for insufflation as part of the surgical procedure, and the escape of the gas must be prevented during puncturing and during the endoscopic surgical procedure. Typically, surgical instruments are inserted into the portal via a valve that has a single, particular size passage dependent upon the puncturing instrument. However, additional instruments to be introduced into the anatomical cavity through the passage may be of diverse types and sizes, and it will be appreciated that fluid can escape past smaller instruments.

A surgical puncturing instrument is usually received within a portal sleeve that passes through the wall of an anatomical cavity with the puncturing instrument and remains in place to establish communication with the interior of the cavity after the puncturing instrument has been removed from the sleeve. The sleeve typically has a proximal end secured in a housing provided with a valve that allows the puncturing instrument to be inserted into the sleeve. The valve prevents the flow of fluids to and from the anatomical cavity and closes when the puncturing instrument is removed from the sleeve. The size of the puncturing instrument utilized varies depending upon the surgical procedure and the type of anatomical cavity to be punctured. Once the puncturing instrument has been removed from the sleeve, a great variety of instruments of various sizes and diameters are introduced into the anatomical cavity via the portal dependent upon the procedure to be performed.

Prior art endoscopic portals utilize a valve, such as a flapper or gate valve, that is normally biased to a closed position but in an open position has a passage or lumen therethrough of only a single size. Accordingly, such endoscopic portals suffer from the disadvantages of allowing the passage or leakage of fluids when surgical instruments smaller than the single passage are introduced therethrough or of limiting the implements to be used in a procedure to a single size. Additionally, such endoscopic portals can be effectively used with only a single size puncturing instrument.

SUMMARY OF THE INVENTION

Accordingly, it is a primary object of the present invention to overcome the above described disadvantages of the prior art by utilizing a valve assembly in an endoscopic portal that provides a variable size passage therethrough to engage surgical instruments of various sizes in sealing relation.

Another object of the present invention is to provide an endoscopic portal with a valve having multiple lumens or passages of diverse sizes for selection to produce a sealing relation with surgical instruments of various sizes.

A further object of the present invention is to provide a valve assembly for an endoscopic portal that normally seals an opening or passage therethrough and allows surgical instruments of diverse sizes to be introduced through the opening or passage while preventing fluid flow or leakage.

The present invention has another object in the use of an elastic or stretchable sleeve in combination with a plurality of spreadable legs to produce a valve for an endoscopic portal having a variable size passage therethrough.

Some of the advantages of the present invention over the prior art are that a complete endoscopic procedure can be performed with a single portal thereby reducing instrument costs and surgery time, a single endoscopic portal can be used with various sizes and types of puncturing instruments, and the endoscopic portal can be inexpensively manufactured to be economically disposable for single patient use.

The present invention is generally characterized in an endoscopic portal including a sleeve or cannula having an open proximal end to provide access to an internal operative site and a valve assembly disposed at the open proximal end of the sleeve for controlling fluid passing therethrough and including a passage of variable size for engaging surgical instruments of various sizes in sealing relation. In one embodiment, the valve assembly includes a plurality of different size lumens or passages that can be selectively aligned with the open proximal end of the sleeve. In another embodiment, the valve assembly stretches or elastically expands to accommodate various size surgical instruments.

Other objects and advantages of the present invention will become apparent from the following description of the preferred embodiment taken in conjunction with the accompanying drawings.

BRIEF DESCRIPTION OF THE DRAWINGS

FIG. 1 is a side view, partly in section, of an endoscopic portal according to the present invention.

FIG. 2 is a section taken along line 2—2 of FIG. 1.

FIG. 3 is a broken view taken along line 3—3 of FIG. 2.

FIG. 4 is a broken side view of the endoscopic portal of FIG. 1.

FIG. 5 is a exploded, perspective view of another valve assembly for the endoscopic portal of the present invention.

FIG. 6 is a broken side view, partly in section, of the valve assembly of FIG. 5 with a surgical instrument passing therethrough.

DESCRIPTION OF THE PREFERRED EMBODIMENTS

With reference to FIG. 1, an endoscopic portal 10 including a valve assembly 12 according to the present invention is shown in combination with a surgical puncturing or penetrating instrument 14 for puncturing penetrating the wall of an anatomical cavity. The puncturing instrument 14 is illustrated as a hollow or tubular needle having an angled, sharp distal end 16; however, any type of puncturing instrument can be utilized in combination with the endoscopic portal 10, such as solid trocars or obturators. The puncturing instrument 14 has a proximal end 18 defining an enlarged handle to allow the puncturing instrument to be withdrawn after insertion.

The endoscopic portal 10 includes a tubular, cylindrical sleeve or cannula 20 for positioning through the body wall during the puncturing procedure to provide access to an internal operative site. The sleeve 20 has a tapered, open distal end 22 adapted to be disposed within the body and an open, proximal end 24 adapted to be disposed externally of the body. The proximal end 24 is externally threaded to engage internal threads at the forward end of a housing 26 to couple the housing with the proximal end of the sleeve. Housing 26 has an enlarged forward flange 28 joined to a tubular end 30 that is internally threaded for receiving the proximal end 24 of sleeve 20. Housing 26 has a generally cylindrical wall 32 extending from flange 28 and terminating at an open, internally threaded end 34, and a valve block 36 is received in end 34. Block 36 has an enlarged flange 38 extending therefrom and an external thread for engaging the internal thread at open end 34 to secure block 36 in the housing. Block 36 is closely received within wall 32 and terminates in a tapered wall 40 positioned adjacent end 30.

A longitudinal passage 42 is defined through the housing including an opening in flange 38 and a bore through block 36 in longitudinal alignment with the longitudinal axis of sleeve 20, and implements such as puncturing instrument 14 can be inserted into sleeve 20 via passage 42. A cylindrical recess 44 is formed in block 36 on an axis transverse to passage 42, and a cylindrical valve body 46 is disposed in recess 44 to be rotatable about its central longitudinal axis which intersects and is oriented transverse to the longitudinal axis of passage 42.

A plurality of different size passages or lumens 48, 50 and 52 are formed in valve body 46 radially with respect to the central longitudinal axis of the valve body. Lumens 48, 50 and 52 have longitudinal axes contained in a common plane, as shown in FIG. 2, which also contains the longitudinal axis of passage 42. Lumens 48, 50 and 52 are angularly spaced from each other and the angular spacing is selected to provide opposing solid surfaces 54 ad 56 on opposite sides of valve body 46 defining arcs of the cylinder large enough in size to cover and seal passage 42 when the solid surfaces 54 and 56 are aligned with passage 42 by rotation of the valve body. Lumens 48, 50 and 52 are of different size or diameter; and, as shown in FIGS. 1 and 2, lumen 50 is the largest diameter passage, lumen 52 is the next largest diameter passage and lumen 48 is the smallest diameter passage.

As depicted in FIGS. 2 and 3, a lower end 58 of valve body 46 has a shaft 60 extending therefrom in longitudinal alignment with the central longitudinal axis of the valve body to project through an opening in a bottom wall 62 of block 36 and terminates at an end surface 64. A slot 66 is formed in end surface 64 to receive one end of a coil spring 68 disposed around shaft 60. A pin 70 projects perpendicularly from wall 62, and the other end of spring 68 abuts pin 70. Spring 68 is rotationally biased to normally maintain valve body 46 in a closed position wherein solid surfaces 54 and 56 on the valve body are aligned with passage 42 to close off the passage and seal the housing 26. The upper end 72 of the valve body is fixed to a cover 74 disposed above housing 26, and an elongated ridge 76 projects from cover 74. In the normally closed position, ridge 76 is oriented transverse to passage 42 as shown in phantom in FIG. 4. Ridge 76 can be manually grasped and rotated in a counter-clockwise direction, looking at FIG. 4, to rotate valve body 46 to an open position corresponding to one of the lumens 48, 50 or 52 being aligned with passage .42 and the open proximal end 24 of sleeve 20. Thus, the first rotational position for valve body 46 aligns lumen 48 with passage 42, the second rotational position for valve body 46 aligns lumen 50 with passage 42, and the third rotational position for valve body 46 aligns lumen 52 with passage 42. Indicia 78 can be provided on the housing 26 to indicate open positions for valve 48 when the ridge 76 is radially aligned with such indicia.

While it is preferred to bias the valve assembly to a normally closed position, bias spring 68 is not required, and the valve body can be held in any of its open positions or its closed position with the use of suitable detents. For example, spring biased ball bearings 80 can be disposed in the block 36 and corresponding recesses 82 can be formed in the valve body 46, or vice versa, as shown in phantom in FIG. 2.

In operation, spring 68 rotationally biases valve body 46 to the closed position where solid surfaces 54 and 56 on the valve body are aligned with passage 42 to seal the housing. Valve body 46 may be rotated by grasping and turning ridge 76 to align the central longitudinal axis of a selected one of the lumens 48, 50 or 52 with the longitudinal axis of passage 42, and an implement such as puncturing instrument 14 having a size corresponding to the size of the aligned lumen can be inserted into the opening in flange 38 to extend through the aligned lumen of the valve body and sleeve 20. Since the aligned lumen corresponds to the size of the inserted implement and the valve body 46 is sealingly received in block 36, the passage of fluids through the housing and valve assembly are prevented. The valve assembly therefore, permits diverse surgical instruments to be inserted into the sleeve with a single portal in a manner maintaining a sealed environment.

When utilized in conjunction with puncturing instrument 14, valve body 46 is rotated to align lumen 50 in valve body 46 with passage 42 in block 36, lumen 50 corresponding in size and cross-sectional shape with puncturing instrument 14 to provide sealing engagement therebetween. The distal end 16 of puncturing instrument 14 is inserted into the housing 26 through the opening in flange 38 to extend through passage 42, lumen 50 and sleeve 20 such that distal end 16 projects from the distal end 22 of the sleeve. For laparoscopy, in many cases, a pneumoperitoneum will have been created, for example with the use of a verres needle. When the puncturing instrument is forced through the anatomical wall, escape of gas from the peritoneum will be prevented due to the seal between the puncturing instrument and the valve assembly. When the puncturing instrument is hollow, such as the illustrated needle, the distal end 18 will be closed to prevent passage of fluid therethrough. If no pneumoperitoneum has been created prior to insertion of the puncturing instrument, insufflation can be accomplished via a valve, not shown, in the proximal end 18 of the needle. Once the anatomical cavity is insufflated and the endoscopic surgical instrument is in place with sleeve 20 passing through the anatomical wall, the puncturing instrument is removed whereupon the spring 68 automatically restores the valve body to the closed position to prevent gas from escaping. Valve body 46 can now be rotated to align the same or a different lumen with passage 42 to allow the same or a different sized surgical instrument to be inserted therethrough for introduction via the sleeve to the operative site.

The number of different size lumens or passages in the valve assembly and the sizes thereof are dependent upon the instruments to be used in the endoscopic procedure to be performed. For example, frequently used instruments commonly have diameters of 3 mm, 5 mm, 7 mm, 10 mm and 12 mm; and, thus, lumens corresponding to these diameters are preferred. By use of indicia 78 on the housing wall 32 in combination with ridge 76, which can act as a pointer or indicator, accurate alignment of a desired lumen can be achieved. By use of detents 80, 82, the accurate alignment of the lumen or passage through the valve assembly with the housing and sleeve can further be assured.

Another embodiment of a valve assembly providing variable passage sizes therethrough in accordance with the present invention is illustrated in FIGS. 5 and 6 and includes a member 84 having a flange 86 adapted to be sealingly mounted in housing 26, for example by providing external threads on the peripheral edge of the flange. A plurality of spaced, spreadable legs 88 extend distally from flange 86 to produce a normally conical configuration tapering to an apex as shown in FIG. 5. The legs 88 and flange 86 are preferably integrally made of unitary construction of a material facilitating movement of medical instruments therethrough and allowing legs 88 to flex, such as a plastic like nylon. The legs 88 are concentrically disposed around a central opening 90 in flange 86 and are slightly spaced from each other as shown by gaps 92 which terminate at curved relief recesses 94. A conical, stretchable sleeve or membrane 96, preferably made of a rubber-like material such as silicone, has a configuration to tightly fit over legs 88 such that the sleeve and legs are normally biased to a closed position at the apex to prevent passage of fluids through the valve assembly.

In use, the valve assembly is normally biased to a closed position due to the elastic force of conical sleeve 96 around legs 88; and, when a surgical instrument 98 is inserted through housing 26 and sleeve 20, the surgical instrument 98 will pass through opening 90 and cause legs 88 to flex outwardly stretching conical sleeve 96 to the position shown in FIG. 6. The conical sleeve acts as a seal to prevent passage of fluids thereby and tightly engages the surgical instrument in the gaps 92 where the legs 88 are spread apart. The valve assembly provides a passage of variable size to accommodate surgical instruments of various sizes passing therethrough in that legs 88 and conical sleeve 96 contract to sealingly engage the surgical instrument regardless of the diameter thereof.

Inasmuch as the present invention is subject to many modifications, variations and changes in detail, it is intended that all subject matter discussed above or shown in the illustrative drawings be interpreted as illustrative only and not to be taken in a limiting sense.

What is claimed is:

1. An endoscopic portal comprising
   a tubular sleeve for insertion through the skin to provide access to an internal operative site for surgical instruments, said sleeve having an open distal end adapted to be disposed within the body and an open proximal end adapted to be disposed externally of the body; and
   valve means disposed at said open proximal end of said sleeve for controlling passage of fluids through said sleeve, said valve means including variable size passage means for communicating with said open proximal end of said sleeve and engaging surgical instruments of various sizes passing therethrough and through said sleeve in sealing relation.

2. An endoscopic portal as recited in claim 1 wherein said passage means includes a plurality of passages of varying size.

3. An endoscopic portal as recited in claim 2 wherein said valve means is movable relative to said open proximal end of said sleeve to permit alignment of individual ones of said plurality of passages with said open proximal end of said sleeve.

4. An endoscopic portal as recited in claim 3 wherein said valve means includes a valve body and said plurality of passages pass through said valve body.

5. An endoscopic portal as recited in claim 4 and further comprising a housing for said valve means coupled with said open proximal end of said sleeve, said valve body being movably mounted in said housing.

6. An endoscopic portal as recited in claim 5 wherein said valve body is rotatably mounted in said housing.

7. An endoscopic portal as recited in claim 6 wherein said valve body has a closed position blocking communication with said open proximal end of said sleeve.

8. An endoscopic portal as recited in claim 7 wherein said valve means includes means biasing said valve body to said closed position.

9. An endoscopic portal as recited in claim 7 wherein said valve body has an axis of rotation and said passages each have an axis disposed transverse to said axis of rotation.

10. An endoscopic portal as recited in claim 9 wherein said valve means includes detent means for maintaining a selected one of said passages in alignment with said open proximal end of said sleeve.

11. An endoscopic portal as recited in claim 1 wherein said passage means includes elastic means normally biased to a closed position blocking communication with said open proximal end of said sleeve and stretchable to engage various size surgical instruments in sealing relation.

12. An endoscopic portal as recited in claim 1 wherein said valve means includes a flange having an opening therein, a plurality of spaced legs disposed around said opening to provide a configuration tapering to an apex axially aligned with said open proximal end of said sleeve, said legs being spreadable to receive surgical instruments of various sizes, and a stretchable membrane surrounding said legs to bias said legs to said tapering configuration and to allow said legs to be spread apart by a surgical instrument while engaging the surgical instrument in sealing arrangement in the spaces between said spread apart legs.

13. An endoscopic portal as recited in claim 12 wherein said legs provide a conical configuration in a normal closed state and said stretchable membrane is made of rubber and has a conical configuration in an unstretched state.

14. An endoscopic portal as recited in claim 1 wherein said valve means includes means biasing said variable size passage means to a closed position.

* * * * *